US012708595B2

(12) United States Patent
Marion et al.

(10) Patent No.: US 12,708,595 B2
(45) Date of Patent: Aug. 18, 2026

(54) CLEANSING COMPOSITIONS WITH NON-MODIFIED CLAY AND POLYGLYCEROL SURFACTANT

(71) Applicant: L'OREAL, Paris (FR)

(72) Inventors: Catherine Marion, Chevilly Larue (FR); Franck Clement, Chevilly Larue (FR); Jeremie Rackelboom, Chevilly Larue (FR); Reda Agnaou, Chevilly Larue (FR)

(73) Assignee: L'OREAL, Paris (FR)

( * ) Notice: Subject to any disclaimer, the term of this patent is extended or adjusted under 35 U.S.C. 154(b) by 571 days.

(21) Appl. No.: 18/258,571

(22) PCT Filed: Dec. 21, 2021

(86) PCT No.: PCT/EP2021/087146
§ 371 (c)(1),
(2) Date: Jun. 21, 2023

(87) PCT Pub. No.: WO2022/136469
PCT Pub. Date: Jun. 30, 2022

(65) Prior Publication Data

US 2024/0033195 A1 Feb. 1, 2024

(30) Foreign Application Priority Data

Dec. 22, 2020 (FR) ...................................... 2013909

(51) Int. Cl.

| | |
|---|---|
| ***A61K 8/00*** | (2006.01) |
| ***A61K 8/04*** | (2006.01) |
| ***A61K 8/26*** | (2006.01) |
| ***A61K 8/34*** | (2006.01) |
| ***A61K 8/39*** | (2006.01) |
| ***A61K 8/44*** | (2006.01) |
| ***A61K 8/73*** | (2006.01) |
| ***A61Q 19/10*** | (2006.01) |

(52) U.S. Cl.
CPC ................ *A61K 8/26* (2013.01); *A61K 8/042* (2013.01); *A61K 8/345* (2013.01); *A61K 8/39* (2013.01); *A61K 8/442* (2013.01); *A61K 8/733* (2013.01); *A61Q 19/10* (2013.01)

(58) Field of Classification Search
None
See application file for complete search history.

(56) References Cited

FOREIGN PATENT DOCUMENTS

| | | | | |
|---|---|---|---|---|
| DE | 2456048 A1 | | 5/1976 | |
| JP | H1045565 A | | 2/1998 | |
| JP | H10330211 A | | 12/1998 | |
| JP | 2003055129 A | | 2/2003 | |
| JP | 2003192532 A | | 7/2003 | |
| JP | 2011038004 A | | 2/2011 | |
| JP | 2017024924 A | | 2/2017 | |
| JP | 2020083764 A | | 6/2020 | |
| WO | WO-2020109500 A1 | * | 6/2020 | ............ A61Q 19/00 |

OTHER PUBLICATIONS

Clay mineral, Earth Sciences, Briatannica Encyclopedia, Sep. 29, 2019 or earlier by Wayback Machine Archive, Retrieved online Sep. 15, 2025, Weblink: <https://www.britannica.com/science/clay-mineral/Kaolin-serpentine-group> (Year: 2019).*
Mineral Data Publishing Hectorite, 2001 (Year: 2001).*
International Search Report and Written Opinion issued on Mar. 14, 2022 for corresponding PCT Application No. PCT/EP2021/087146.
Preliminary Search Report issued on Oct. 25, 2021 for corresponding French Application No. 2013909.
Abdelaziz Benhammou et al.; "Mineralogical and Physicochemical Investigation of Mg-Smectite from Jbel Ghassoul, Morocco," Clays and Clay Minerals, vol. 57, No. 2, 2009, pp. 264-270 XP055851956.

* cited by examiner

*Primary Examiner* — Necholus Ogden, Jr.
(74) *Attorney, Agent, or Firm* — POLSINELLI PC

(57) ABSTRACT

An object of the present invention is a cosmetic composition, in particular for cleansing the skin and/or skin appendages, comprising, in an aqueous physiologically acceptable medium:

at least one non-modified clay selected from trioctahedral smectites, and at least one ester selected from esters of fatty acid comprising from 4 to 16 carbon atoms and polyglycerol comprising from 2 to 10 glycerol units, the ester:clay weight ratio being strictly greater than 1.

19 Claims, No Drawings

CLEANSING COMPOSITIONS WITH NON-MODIFIED CLAY AND POLYGLYCEROL SURFACTANT

CROSS-REFERENCE TO RELATED APPLICATIONS

This application is a national stage application (under 35 U.S.C. § 371) of PCT/EP2021/087146, filed Dec. 21, 2021, which claims the benefit of French Application No. 2013909, filed Dec. 22, 2020, disclosures of which are incorporated herein by reference in their entirety.

The present invention relates to cleansing compositions with clay.

The cleansing of the skin is very important for skin care. It must be as effective as possible because fatty residues such as excess sebum or the remainder of cosmetic products used daily accumulate in the skin folds and can obstruct the pores of the skin and cause the appearance of pimples. An effective cleansing of the skin is carried out in particular using foaming products.

Foaming cleansing products currently commercially available have the form of cakes, gels or foaming liquids. They generally contain either soaps, which have the advantage of providing a creamy and voluminous foam, or an association of foaming surfactants and stabilizers. In particular, the compositions in the form of gels often comprise water, a water-soluble polymer and a mixture of surfactants. Loads can also be added to the composition in order to provide an anti-oily skin effect; indeed, these loads are deposited on the skin, absorb the sebum and/or perspiration, and thus maintain a matteness effect of the face. The latter particularly include clays.

However, the current compositions have a high content in clay(s), which can lead to problems of sedimentation which have a harmful effect on the sensory properties of the compositions.

There is therefore a need to have cleansing compositions of human keratin materials, preferably the skin of the face and/or of the body and/or of the hair, having a satisfactory foamy texture, in particular a creamy foam, while still being stable and having good cleansing properties. There is also the need to have cleansing compositions that have anti-oily skin properties and of which the stability is improved, in particular of which the problems of sedimentation are reduced. In particular, there is a need for foaming cleansing compositions that have little or no syneresis.

The purpose of this invention is to propose such compositions. The compositions according to the invention do not have the disadvantages of the prior art, in particular they have good qualities of use (quality and creaminess of foam, anti-oily skin effect), and are stable (i.e. no syneresis).

Indeed, the inventors have demonstrated that the association of a non-modified clay selected from trioctahedral smectites and a short-chain polyglycerol surfactant (i.e. in C4-C16), makes it possible to obtain a cosmetic composition that meets these needs.

Therefore, an object of the present invention is a cosmetic composition, in particular for cleansing the skin and/or skin appendages, comprising in an aqueous physiologically acceptable medium:

- at least one non-modified clay selected from trioctahedral smectites,
- and at least one ester selected from esters of fatty acid comprising from 4 to 16 carbon atoms and polyglycerol comprising from 2 to 10 glycerol units, the ester:clay weight ratio being strictly greater than 1.

Another object of the present invention is a method for cleansing the skin and/or skin appendages, comprising the application on the skin and/or skin appendages of a composition according to the invention.

"Physiologically acceptable medium" means a medium compatible with skin and/or skin appendages.

Non-Modified Clay

The composition according to the invention comprises at least one non-modified clay selected from trioctahedral smectites.

This clay belongs to the phyllosilicates that have a structure in sheets 2:1. The classification of clays is referenced in the following work: Bergaya F., Lagaly G. "Handbook of Clay Science" 2nd Edition. A. Fundamentals—Elsevier Ltd., 2013.

Phyllosilicates are minerals of the group of silicates constructed by stacking tetrahedral layers ("T") where the tetrahedrons share three summits out of four (the "basal" oxygens), the fourth summit (the "apical" oxygen) being connected to an octahedral layer ("O") occupied by different cations. In phyllosilicates that have a TOT structure, an octahedral layer O is inserted between two tetrahedral layers T.

The 2:1 sheet structure is also called TOT structure, T being a tetrahedral layer and O being an octahedral layer.

The non-modified clay according to the invention belongs to the smectites.

The structure of the smectites is distinguished from other phyllosilicates that have a structure in 2:1 sheets by the presence of an interfoliar space between each association of TOT sheets that depends on the state of hydration of the clay, and wherein interfoliar cations are inserted. Smectites are often called "swelling" clays. Preferably, the interfoliar cations are selected from $Ca^{2+}$, $Mg^{2+}$, $Na^{+}$ and $Li^{+}$.

The non-modified clay according to the invention is selected from trioctahedral smectites.

Trioctahedral smectites are characterized by the fact that all the octahedral sites of the TOT structure are mainly occupied by divalent cations. Preferably, the divalent cations of the octahedral sites are selected from $Mg^{2+}$ and $Fe^{2+}$.

In particular, the non-modified clays according to the invention are trioctahedral smectites that can be exfoliated or "activated" in the presence of water, thus forming aqueous gels due to the existence of interfoliar cations within the structure.

When the water comes into contact with a non-modified clay that is suitable for the invention, it hydrates the sheets of the latter, thus inducing a swelling of the distance between the sheets. Then, a separation of the sheets possibly takes place via an exfoliation and/or delamination mechanism. An aqueous gel is then obtained. It is essentially a content ranging from 0.5% to 10% by weight, with respect to the total weight of the composition, of this specific type of clay, that makes it possible to obtain gelled aqueous phases in the compositions according to the invention.

Preferably, the clay according to the invention comprises a quantity by weight of $SiO_2$ greater than or equal to 30% with respect to the total weight of the clay, preferably comprised between 35% and 65% by weight, and a quantity by weight of MgO greater than or equal to 10%, preferably comprised between 15% and 30% by weight. According to a preferred embodiment, the clay according to the invention comprises from 35% to 65% by weight of $SiO_2$, with respect to the total weight of the non-modified clay, and from 15% to 30% by weight of MgO, with respect to the total weight of the non-modified clay.

Preferably, in the clay according to the invention, the $SiO_2/MgO$ weight ratio is comprised between 1 and 3, preferably between 1.5 and 2.5, preferably between 1.8 and 2.4.

Preferably, the clay according to the invention further comprises a quantity by weight of $Al_2O_3$ comprised between 0% and 15% with respect to the total weight of the clay.

According to a first alternative, a clay suitable for the invention is devoid (free) of $Al_2O_3$.

According to a second alternative, a clay suitable for the invention can comprise from 0.1% to 15% by weight of $Al_2O_3$, preferably from 8% to 12% by weight, with respect to the total weight of the non-modified clay.

According to another preferred embodiment, when the $Al_2O_3$ is present within the clay suitable for the invention, the $SiO_2/Al_2O_3$ weight ratio is strictly greater than 3.

Preferably, the clay according to the invention has a density less than 2.7. The density (or specific gravity) is a very important property of minerals; the calculation thereof is rather simple. It has no unit, and is measured using various devices and techniques that are covered in most mineralogy manuals. Among these methods, the Jolly balance and the beam balance are the best suited for the work on mineral samples. The device for taking these measurements is simple and can be constructed at low cost (Sinkankas, 1966). Density meets the following calculation:

Densité=(poids dans l'air)/(poids dans l'air–poids dans l'eau). [Math 1]

According to a particular embodiment, a non-modified clay suitable for the invention has the following general molecular formula:

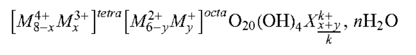

$$[M^{4+}_{8-x}M^{3+}_{x}]^{tetra}[M^{2+}_{6-y}M^{+}_{y}]^{octa}O_{20}(OH)_4X^{k+}_{\frac{x+y}{k}},\ nH_2O$$

wherein $M^{4+}$ represents a cation, preferably $Si^{4+}$, $M^{3+}$ represents a cation, preferably $Al^{3+}$, $M^{2+}$ represents a cation, preferably $Fe^{2+}$ or $Mg^{2+}$, $M^{+}$ represents a cation, preferably $Li^{+}$, X represents an interfoliar cation, preferably $Ca^{2+}$, $Na^{+}$, $Li^{+}$, or mixtures thereof, x represents the tetrahedral substitution rate, y represents the octahedral substitution rate, k represents the valency of the interfoliar cation X, n represents an integer, preferably from 0 to 100.

The non-modified clay suitable for the invention is generally available in powder form.

Preferably, the non-modified clay is selected from non-modified hectorite, non-modified stevensite and non-modified saponite.

Advantageously, the non-modified clay is non-modified hectorite. The non-modified hectorite can be defined by the following formula: $Na_x(Mg_{3-x},Li_x)Si_4O_{10}(OH)_2$, x being comprised between 0.2 and 0.4, preferably equal to 0.3.

Preferably, the clay of the composition according to the invention is different from sauconite, sobotkite, talc and montmorillonite.

The term non-modified clay means a natural or synthetic clay that has not been subjected to any modification of any type whatsoever. For example when a non-modified clay suitable for the invention is a non-modified hectorite, the latter is different from hectorites modified by a $C_{10}$ to $C_{22}$ fatty acid ammonium chloride, such as the hectorite modified by distearyl dimethyl ammonium chloride. According to an embodiment, a non-modified clay suitable for the invention is synthetic.

According to a preferred embodiment, a non-modified clay suitable for the invention is natural, preferably natural hectorite.

The term modified clay means silicates in sheets of which the lipophilicity has been increased, for example by ion exchange reactions with quaternary ammonium salts, preferably quaternary ammonium chlorides. The quaternary ammonium chlorides are for example benzyldimethylstearylammonium chloride, or quaternium-18, of formula

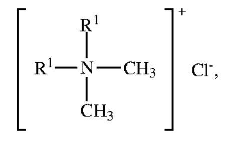

wherein the $R^1$ groups are independently selected from C12-C20 saturated linear alkyl groups. Modified clays are for example disteardimonium hectorite or stearalkonium hectorite.

Preferably, the composition according to the invention is substantially free from modified clay, preferably substantially free from disteardimonium hectorite and stearalkonium hectorite. "Substantially free" means that the composition comprises less than 0.1% by weight in relation to the total weight of the composition, preferably less than 0.05% by weight, preferably less than 0.01% by weight of modified clay. Preferably, the composition according to the invention is completely free from modified clay.

Preferably, the clay is present with a content of between 0.1% and 10% by weight in relation to the total weight of the composition, preferably between 0.5% and 8% by weight, preferably between 1% and 5% by weight, advantageously between 1.5% and 3%.

As a non-modified clay and more particularly non-modified hectorite, use can in particular be made of that marketed by Elementis under the name Bentone EW or HYDROCLAY 2000 LO.

Fatty Acid and Specific Polyglycerol Ester

The composition according to the invention also comprises at least one ester selected from the esters of fatty acid comprising 4 to 16 carbon atoms and of polyglycerol comprising 2 to 10 glycerol units.

Preferably, the ester selected from the esters of fatty acid comprising 4 to 16 carbon atoms and polyglycerol ester comprising 2 to 10 glycerol units according to the invention is a mono- or di-ester, preferably a mono-ester.

The term "polyglycerol" denotes glyceryl polymers that are linear chains of glycerol units.

The esters that are more particularly considered according to the present invention are esters resulting from the esterification of polyglycerol and carboxylic acid(s) having a carbon chain of a given length.

The carboxylic acid may be linear or branched, saturated or unsaturated.

Preferably, it is a linear monocarboxylic acid.

In general, they are derived from the esterification of at least one hydroxyl function of a polyglycerol by a carboxylic acid having a carbon chain of a given length.

According to one particular embodiment, esters suitable for this invention can be derived from esterification of a polyglycerol by one or more identical or different carboxylic acids. It may be a hydroxylated mono-ester, a hydroxylated di-ester, a hydroxylated tri-ester, or a mixture thereof.

The ester is formed (i) from at least one fatty acid comprising an alkyl or alkenyl chain comprising 4 to 16 carbon atoms (also called C4 to C16 fatty acids), and (ii) 2 to 10 glycerol units.

Preferably, the fatty acid comprises 6 to 14 carbon atoms, preferably 8 to 12 carbon atoms. Preferably the fatty acid is saturated and contains a linear alkyl chain.

Preferably, the fatty acid comprising 4 to 16 carbon atoms such is selected from capric acid, lauric acid, myristic acid and palmitic acid.

Preferably the fatty acid is C10, preferably it is capric acid.

Preferably, the ester comprises 3 to 6 glycerol units, preferably 4 glycerol units.

In a preferred embodiment of the invention, the ester is an ester of fatty acid comprising 10 carbon atoms and of polyglycerol comprising 4 glycerol units.

More preferably, the ester is polyglyceryl monocaprate comprising 4 glycerol units, i.e. polyglyceryl-4 monocaprate.

A commercial product mostly based on polyglyceryl-4 monocaprate or PG-4 caprate is available under the tradename TEGOSOFT PC 41 from the company EVONIK GOLDSCHMIDT.

According to another embodiment of the invention, the ester is an ester of fatty acid comprising 12 carbon atoms and of polyglycerol comprising 5 glycerol units, preferably polyglyceryl monolaurate comprising 5 glycerol units, i.e. polyglyceryl-5 monolaurate. A commercial product mostly based on polyglyceryl monolaurate or PG-5 laurate is available under the tradename SUNSOFT A-121E-C® by the company Taiyo Kagaku.

The fatty acid and polyglycerol ester may be present in the composition according to the invention in a content ranging from 0.5% to 10% by weight relative to the total weight of the composition, preferably from 1% to 8% by weight, and more preferably from 2% to 6% by weight.

According to the invention, the weight ratio (ester:clay) of the composition is strictly greater than 1. Preferably, it is greater than or equal to 1.05, preferably greater than or equal to 1.5, preferably greater than or equal to 1.8.

Polymer

The polymers that can be used in the compositions according to the invention are for example oligo- or polysaccharides, acrylic and/or methacrylic polymers or copolymers, carboxyvinyl polymers, polyglyceryl acrylates or methacrylates.

As particular polymers, mention can be made of the carboxyvinyl polymers sold under the tradename CARBOPOL by the company GOODRICH or SYNTHALEN K by the company SIGMA, acrylic acid/ethyl acrylate copolymers, stearyl acrylic/methacrylate acid copolymers, polyglycerylmethacrylate sold under the tradename LUBRAJEL by the company GUARDIAN or polyglycerylacrylate sold under the tradename HISPAGEL by the company HISPANO CHIMICA.

Preferably, the composition of the invention comprises at least one polysaccharide or an oligosaccharide, preferably at least one polysaccharide. This polysaccharide is a hydrophilic thickening polymer.

Preferably, the polysaccharide is selected from natural polymers such as cellulose derivatives such as carboxymethylcellulose, hydroxyethylcellulose, hydroxypropylcellulose, hydroxymethylcellulose, hydroxypropylmethylcellulose, ethylhydroxyethylcellulose, xanthan gum, carob gum, arabic gum, acacia gum, natural and modified cationic scleroglucans, gellan, konjac, rhamsan gums, alginates, pectins, karaya gum, modified or non-modified starch, carrageenans, galactomannans, pullulans, modified or non-modified guar gums and the derivatives thereof such as hydroxypropylguar, hyaluronic acid salts such as sodium hyaluronate, arabinogalactans such as arabic gum, exopolysaccharides (polysaccharides of microbial origin) including xanthan gum or dextran, fructans such as inulin, agar-agar.

Preferably, the oligosaccharide is selected from diholosides or triholosides, such as in particular diholosides or triholosides of cellobiose, gentiobiose, inulobiose, isomaltose, isomaltulose, kojibiose, lactose, laminaribiose, leucrose, maltose, maltulose, melibiose, nigerose, robinose, rutinose, saccharose, sophorose, trehalose, trehalulose, turanose, erlose, fucosyllactose, gentianose, inulotriose, 1-kestrose, 6-kestrose, maltotriose, mannotriose, melezitose, neokestose, panose, raffinose, rhamninose, cyclodextrine, stachyose or verbascose.

Preferably, the composition of the invention comprises at least one polysaccharide, and this polysaccharide is selected from alginates and natural gums such as xanthan gum.

The polymer, preferably polysaccharide, can be present in the composition according to the invention in a content ranging from 0.1% to 10% by weight, with respect to the total weight of the composition, preferably ranging from 0.5% to 7% by weight, and preferably ranging from 0.7% to 3% by weight.

Aqueous Phase

The composition according to the invention comprises a physiologically acceptable aqueous phase, which forms a physiologically acceptable aqueous medium.

The composition according to the invention preferably comprises an aqueous phase comprising water and optionally one or more organic solvent(s) soluble in water at 25° C. These solvents can advantageously be selected for example from linear or branched alkanols, in C2-C4, such as ethanol and isopropanol, propanol, butanol; polyols particularly with 2 to 20 carbon atoms, preferably 2 to 6 carbon atoms. This polyol can be selected from glycerin and derivatives thereof, and glycols and derivatives thereof. The polyol can be selected from the group composed of glycerin, diglycerin, polyglycerin, diethylene glycol, propylene glycol, dipropylene glycol, butylene glycol, pentylene glycol, hexylene glycol, 1,3-propanediol, 1,5-pentanediol, octane 1,2-diol, polyethyleneglycols, particularly having from 5 to 50 ethylene oxide groups, and sugars such as sorbitol, and mixtures thereof.

The composition generally comprises from 40% to 98% by weight of water with respect to the total weight of the composition, preferably from 60% to 95% by weight, preferably from 70% to 93% by weight.

The amount of organic solvent(s) can range for example from 0.01 to 15% by weight, preferably from 0.5% to 13% by weight, still better from 1 to 10% by weight relative to the total weight of the composition.

Preferably, the composition according to the invention is an aqueous gel.

Furthermore, the composition according to the invention can comprise one or more conventional cosmetic additives in particular selected from fatty substances, softeners, antioxidants, active agents, stabilizers, sequestrants, moisturizing agents, vitamins, scents, preservatives, alkalizing agents or acidifiers or any other ingredient usually used for cosmetics and/or dermatology, in particular for the manufacture of compositions in the form of aqueous gels.

Preferably, the composition according to the invention is substantially free of polymer of synthetic origin. "Substantially free" means that the composition comprises less than 1% by weight, preferably less than 0.5% by weight, preferably less than 0.1% by weight with respect to the total weight of the composition, of synthetic polymer origin. Preferably, the composition according to the invention is completely free of polymer of synthetic origin.

Preferably, the composition according to the invention is substantially free of alkylpolyglycoside surfactant. "Substantially free" means that the composition comprises less than 1% by weight, preferably less than 0.5% by weight, preferably less than 0.1% by weight with respect to the total weight of the composition, of alkylpolyglycoside surfactant. Preferably, the composition according to the invention is totally free of alkylpolyglycoside surfactant.

Another object of the present invention is a method for cleansing the skin and/or skin appendages, comprising the application on the skin and/or skin appendages of a composition according to the invention. Preferably, the composition is rinsed.

Consequently, preferably, the method for cleansing the skin and/or skin appendages according to the invention comprises the application on the skin and/or skin appendages of a composition according to the invention, then the rinsing of the skin and/or skin appendages.

The expressions "between . . . and . . . ", "ranging from . . . to . . . " and "varies from . . . ", " . . . to . . . " are to be understood to be inclusive of the limits, unless specified otherwise.

Concrete, yet non-limiting, examples, illustrating the invention, will now be provided.

Unless stated otherwise, the pressure in the examples is atmospheric pressure.

Unless specified otherwise, the % are expressed by weight in relation to the total weight of the composition (% w/w).

EXAMPLES

Example 1: Characterization of a Natural Non-Modified Clay According to the Invention A/ Aqueous gels are prepared according to the following protocol:

1. Preparation of mixtures of water and 2% by weight of active substance for each one of the ingredients in table 1 hereinbelow: mixing under rayneri (rotor/stator) for 10 min at 3,000 rpm;
2. Samples carried out via dilution: or mixing in the mixer for 3 min at 3,500 rpm (100 g);
3. Observation/taking of photos and rheological measurements at t=24 h (except for montmorillonite).

TABLE 1

| Clay | INCI name and supplier |
|---|---|
| Non-modified hectorite | HECTORITE (Elementis) |
| Modified hectorite | DISTEARDIMONIUM HECTORITE (Elementis) |
| Montmorillonite | MONTMORILLONITE (BYK ADDITIVES & INSTR.) |
| Mica | MICA (BASF) |
| Talc | TALC (IMERYS) |

TABLE 1-continued

| Clay | INCI name and supplier |
|---|---|
| Kaolin | KAOLIN (IMERYS) |
| Rassoul or Ghassoul | MOROCCAN LAVA CLAY (GREENTECH) |

The results are as follows:

TABLE 2

| Clay | Result of the mixture/ formation of gel at t = 24 h |
|---|---|
| Non-modified hectorite | Formation of aqueous gel |
| Modified hectorite | No formation of gel Sedimentation |
| Montmorillonite | No formation of gel |
| Mica | No formation of gel Sedimentation |
| Talc | No formation of gel Sedimentation |
| Kaolin | No formation of gel Sedimentation |
| Rassoul or Ghassoul | No formation of gel Sedimentation |

These results demonstrate that only the non-modified hectorite according to the invention is capable of forming a composition in the form of an aqueous gel.

Example 2: Evaluation of the Sebum Absorption Properties of a Composition According to the Invention with Respect to a Comparative Composition Composition C1 according to the invention, and the comparative composition C* are prepared with the ingredients mentioned in the table hereinbelow according to the following protocol:

The hectorite or the kaolin is dispersed in the water/glycerine mixture heated to 60° C. using a rotor stator for 10 minutes. It is cooled to ambient temperature. The sodium alginate is dispersed with the rotor stator, it is hydrated for 5 minutes. Finally, the surfactants are added, then the preservatives and scent.

TABLE 3

| Ingredient | C1 (% w/w) (invention) | C* (% w/w) (comparative) |
|---|---|---|
| Non-modified hectorite (Bentone EW ELEMENTIS) | 2.3 | — |
| Non-modified kaolin (KAOLIN SUPREME IMERYS) | — | 2.3 |
| Sodium alginate | 1.2 | 1.2 |
| Glycerin | 10 | 10 |
| Polyglyceryl-4-caprate | 2.5 | 2.5 |
| Sodium cocoyl glutamate at 25% in water | 8 | 8 |
| Preservatives | Qs | Qs |
| Perfume | 0.2 | 0.2 |
| Water | Qs 100 | Qs 100 |

The sebum absorption properties of the compositions C1 and C* were evaluated. The following test protocol models the change over time of the compositions with respect to a sebum/sweat mixture on the skin:

1) A sebum/sweat mixture that is close to the hydrolipidic film of the skin is modeled by preparing a Vichy spring water/oleic acid/Oleth-10 mixture (respective weight ratio: 79/20/1).

2) A 100 μm thick film is spread over the DURAPORE hydrophobic filter with 0.22 μm GVHP membrane filters (commercial reference: GVHP00010) using an automatic applicator. The film is dried 24 h in an oven at 40° C.

3) The brightness of the film after drying is measured using the brightness-meter (BYK) at 4) The Vichy spring water/oleic acid/Oleth-10 mixture is sprayed on the film once said mixture has returned to ambient temperature.

5) The brightness of the film is measured using a brightness-meter (BYK) at 60° after 6 min after spraying, then the film is again sprayed, and the brightness is again measured 6 min after this second spraying, then the film is sprayed a third time, and the brightness is again measured 6 min after this third spraying. The values measured are called unit of brightness UB.

6) A performance index is calculated, which makes it possible to quantify the performance of the compositions C1 and C*.

For comparison, a negative reference (Gel with amino-propane-sulfonic acid—AMPS—without load, index=0) and a positive reference (AMPS gels with 2% aerogel, index=100) were selected.

Thus, for each composition, the index is calculated to position it on a scale from 0 to 100. If the index is greater than 100, this means that the composition tested is even more effective than the positive reference.

The index is calculated using the following formula:

$$\text{Index}\ (\mathit{Compo\ Cx},\ T6\ \text{min}) = \frac{UB\ (\mathit{Compo\ Cx},\ T6\ \text{min}) - UB\ (\mathit{réf\ négative},\ T6\ \text{min})}{UB\ (\mathit{réf}\ \text{positive},\ T6\ \text{min}) - UB\ (\mathit{réf\ négative},\ T6\ \text{min})}$$

The results obtained are indicated in the following table:

TABLE 4

| Composition | UB T0 Film | UB T6 min | Performance T 6 min | UB T12 min | Performance T 12 min | UB T18 min | Performance T 18 min |
|---|---|---|---|---|---|---|---|
| Positive Ref | 3.1 | 3 | 100 | 3 | 100 | 3 | 100 |
| Negative Ref | 44.7 | 36.9 | 0.0 | 29.9 | 0.0 | 32.9 | 0.0 |
| C* (comparative) | 11.1 | 19.6 | 51.0 | 24.2 | 21.2 | 26.8 | 20.4 |
| C1 (invention) | 6.4 | 9.2 | 81.7 | 11.8 | 67.3 | 17.6 | 51.2 |

The first column of values corresponds to the brightness of the dry film before spraying the solution. The second value is the brightness 6 minutes after the first spraying, followed in the third column by the corresponding performance index. The 4th column of values corresponds to the brightness 6 minutes after the second spraying. The 6th column of values corresponds to the brightness 6 minutes after third spraying.

This results in that the value of brightness varies substantially when the clay used is kaolin, leading to average to low performance indexes according to the number of sprayings. With hectorite, the brightness increases much more strongly. The performance index of the formula according to the invention C1 is very good after the first spraying, and remains satisfactory afterwards. Hectorite is therefore able to absorb a quantity of artificial sebum that is much greater than kaolin, with a clearly lower impact on the brightness of the film (and therefore the skin).

Example 3: Evaluation of the Foaming Properties of a Composition According to the Invention with Respect to Comparative Compositions Composition F1 according to the invention and the comparative compositions F2 to F4 are prepared with the ingredients mentioned in the table hereinbelow according to the protocol of example 2.

These compositions are all gels.

TABLE 5

| Ingredient | F1 (% w/w) (invention) | F2 (% w/w) (comparative) | F3 (% w/w) (comparative) | F4 (% w/w) (comparative) |
|---|---|---|---|---|
| Non-modified hectorite (HYDROCLAY 2000 LO, Elementis) | 2.5 | 2.5 | 2.5 | 2.5 |
| Sodium alginate | 0.8 | 0.8 | 0.8 | 0.8 |
| Polyglyceryl-4-caprate (TEGOSOFT PC 41 from EVONIK GOLDSCHMIDT) | 5 | 0 | 0 | 0 |
| Sodium cocoyl glycinate (AMILITE GCS-12K, Ajinomoto) (*30% a.s. in water) | 0 | 0 | 0 | 16.67 (* 5% a.s.) |
| Caprylyl/capryl glucoside (ORAMIX CG 110L, Seppic) (*60% a.s. in water) | 0 | 8.33 (* 5% a.s.) | 0 | 0 |
| Potassium laurate (POTASSIUM LAURATE (DUB LK), Stéarinerie DUBOIS) | 0 | 0 | 5% | 0 |
| Water | qs 100 | qs 100 | qs 100 | qs 100 |

a.s.: active substance

The gels were evaluated for their foamy texture (firmness). "Firmness" means the force required to reach a predefined deformation of the surface of the product tested. This force is expressed in grams (g). The firmness measurements were taken with the TA.XT plus brand texturometer from the company Stable Micro Systems.

The test was conducted in the following way:

Foam Generation:

In a 400 ml beaker, 30 g of the formula is diluted 3 times in tap water.

Then a Braun (600 w Turbo) mixer is used—speed 1 position 15, to generate the foam.

The density of the foam is then measured with the texturometer:

The measurements are taken with the TA.XT plus brand texturometer from the company Stable Micro Systems via extrusion with a set: plexiglas jar with reference A/EB (diameter mm)+piston (diameter 45 mm).

Immediately after the generation of foam at time T=2 min, the foam extrusion jar is filled with a marysette, it is leveled then weighed.

Measurement protocol: Measurement threshold: 5 g, Travel: 40 mm, Rate of descent of the sensor: 40 $mm \cdot s^{-1}$, Measurements: Retro-extrusion.

The results are presented in the following table:

TABLE 6

| Formula | Texture/firmness of the foam: pressure (g) at extrusion | |
|---|---|---|
| F1 (invention) | 187.7 | +/−1.0 |
| F2 (comparative) | 172.8 | +/−5.3 |
| F3 (comparative) | 147.9 | +/−3.9 |
| F4 (comparative) | 178.2 | +/−7.7 |

The higher the measured value is, the firmer the foam obtained is, and the creamier the application of the production will be.

It is observed that the highest value is obtained for polyglyceryl-4-caprate (formula F1 according to the invention). In comparison with the other surfactants evaluated, the texture obtained with polyglyceryl-4-caprate is therefore the creamiest.

The invention claimed is:

1. A cosmetic composition which is an aqueous gel comprising, in an aqueous physiologically acceptable medium:

at least one non-modified clay selected from trioctahedral smectites, and at least one mono-ester selected from mono-esters of fatty acid comprising from 4 to 16 carbon atoms and polyglycerol comprising from 2 to 10 glycerol units, the mono-ester:clay weight ratio being strictly greater than 1.

2. The composition according to claim 1, wherein the non-modified clay comprises a quantity by weight of $SiO_2$ greater than or equal to 30% with respect to the total weight of the clay; and a quantity by weight of MgO greater than or equal to 10%.

3. The composition according to claim 2, wherein the non-modified clay comprises a $SiO_2$/MgO weight ratio between 1 and 3.

4. The composition according to claim 1, wherein the non-modified clay further comprises a quantity by weight of $Al_2O_3$ between 0% and 15% with respect to the total weight of the clay.

5. The composition according to claim 1, wherein the non-modified clay is selected from non-modified hectorite, non-modified stevensite and non-modified saponite.

6. The composition according to claim 1, wherein the non-modified clay is present in a content of between 0.1% and 10% by weight in relation to the total weight of the composition.

7. The composition according to claim 1, wherein the mono-ester is formed (i) from at least one fatty acid comprising an alkyl or alkenyl chain containing 4 to 16 carbon atoms and (ii) 2 to 10 glycerol units.

8. The composition according to claim 1, wherein the mono-ester of fatty acid comprising 10 carbon atoms and of polyglycerol comprising 4 glycerol units.

9. The composition according to claim 1, wherein the mono-ester is present in a content ranging from 0.5% to 10% by weight, with respect to the total weight of the composition.

10. The composition according to claim 1, wherein the mono-ester:clay weight ratio is greater than or equal to 1.05.

11. The composition according to claim 1, which comprises at least one polymer selected from oligo- or polysaccharides, acrylic and/or methacrylic polymers or copolymers, carboxyvinyl polymers, polyglyceryl acrylates or methacrylates.

12. The composition according to claim 1, wherein the aqueous medium comprises water and optionally one or more water-soluble organic solvent(s) at 25° C.

13. A method for cleansing the skin and/or skin appendages, comprising the application on the skin and/or skin appendages of a composition according to claim 1.

14. The composition according to claim 2, wherein the non-modified clay further comprises a quantity by weight of $Al_2O_3$ between 0% and 15% with respect to the total weight of the clay.

15. The composition according to claim 3, wherein the non-modified clay further comprises a quantity by weight of $Al_2O_3$ between 0% and 15% with respect to the total weight of the clay.

16. The composition according to claim 2, wherein the non-modified clay is selected from non-modified hectorite, non-modified stevensite and non-modified saponite.

17. The composition according to claim 3, wherein the non-modified clay is selected from non-modified hectorite, non-modified stevensite and non-modified saponite.

18. The composition according to claim 4, wherein the non-modified clay is selected from non-modified hectorite, non-modified stevensite and non-modified saponite.

19. The composition according to claim 2, wherein the non-modified clay is present in a content of between 0.1% and 10% by weight in relation to the total weight of the composition.

* * * * *